(12) United States Patent
Taylor et al.

(10) Patent No.: US 6,656,160 B1
(45) Date of Patent: *Dec. 2, 2003

(54) INSUFFLATION NEEDLE APPARATUS

(75) Inventors: Scott Taylor, Mission Viejo, CA (US);
Gary Johnson, Mission Viejo, CA (US); Nabil Hilal, Mission Viejo, CA (US)

(73) Assignee: Applied Medical Resources Corporation, Rancho Santa Margarita, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/844,113

(22) Filed: Apr. 29, 1997

(51) Int. Cl.[7] .............................................. A61M 5/178
(52) U.S. Cl. ........................ 604/158; 604/23; 604/264; 606/185
(58) Field of Search ......................... 604/158, 51, 164, 604/274, 26, 23, 170, 264, 19, 160, 166, 161, 164.01, 164.08, 164.11, 164.12, 166.01, 170.01, 171.02, 171, 506, 169, 272; 600/567; 606/185

(56) References Cited

U.S. PATENT DOCUMENTS

| 2,630,803 | A |   | 3/1953  | Baran ........................... 128/221 |
|-----------|---|---|---------|-----------------------------------------|
| 4,180,068 | A |   | 12/1979 | Jacobsen et al. ........... 128/214 R    |
| 4,666,438 | A | * | 5/1987  | Raulerson ..................... 604/272  |
| 4,735,215 | A | * | 4/1988  | Goto et al. ................... 128/754  |
| 4,808,168 | A | * | 2/1989  | Warring ........................ 604/158 |
| 4,808,170 | A | * | 2/1989  | Thornton et al. ............ 604/274     |
| 4,869,717 | A |   | 9/1989  | Adair ........................... 604/51 |
| 4,874,375 | A | * | 10/1989 | Ellison ......................... 604/164 |
| 5,057,085 | A | * | 10/1991 | Kopans ......................... 604/173 |
| 5,098,388 | A |   | 3/1992  | Kulkashi et al. ............. 604/158    |
| 5,104,381 | A |   | 4/1992  | Gresl et al. .................. 604/164  |
| 5,137,509 | A |   | 8/1992  | Freitas ......................... 604/26 |
| 5,256,148 | A |   | 10/1993 | Smith et al. ................. 604/158   |
| 5,258,003 | A |   | 11/1993 | Ciaglia et al. ............... 606/185   |
| 5,275,611 | A | * | 1/1994  | Behl ........................... 606/198 |
| 5,284,474 | A |   | 2/1994  | Adair .......................... 604/164 |
| 5,300,084 | A |   | 4/1994  | Johnson ....................... 606/185  |
| 5,320,608 | A | * | 6/1994  | Gerrone ....................... 604/117  |
| 5,364,365 | A | * | 11/1994 | Wortrich ...................... 604/158  |
| 5,374,252 | A | * | 12/1994 | Banks et al. ................. 604/158   |
| 5,421,821 | A |   | 6/1995  | Janicki et al. ................ 604/26   |
| 5,454,790 | A | * | 10/1995 | Dubrul ......................... 604/104 |
| 5,514,087 | A | * | 5/1996  | Jones .......................... 604/26  |
| 5,514,111 | A |   | 5/1996  | Phelps ......................... 604/248 |
| 5,562,611 | A | * | 10/1996 | Transue ........................ 604/26  |
| 5,667,514 | A | * | 9/1997  | Heller ......................... 604/108 |
| 5,669,543 | A | * | 9/1997  | Ueno ........................... 227/67  |
| 5,669,883 | A | * | 9/1997  | Scarfone et al. ............ 604/167     |
| 5,735,828 | A | * | 4/1998  | Jungnelius ................... 604/264   |
| 5,735,865 | A | * | 4/1998  | Schaumann et al. ......... 606/167       |
| 5,741,284 | A | * | 4/1998  | Karlsson ...................... 604/160  |

* cited by examiner

Primary Examiner—Brian L. Casler
Assistant Examiner—Cris L. Rodriguez
(74) Attorney, Agent, or Firm—Richard L. Myers (57) ABSTRACT

Apparatus for insufflating a body conduit or cavity includes a needle having a lumen defined by an inner surface and a sharp distal tip. An obturator, disposed within the lumen of the needle and movable axially between a proximal position and a distal position, includes an extension member which defines an insufflation channel with the inner surface of the needle. A blunt distal terminus on the extension member is disposed distally of the sharp tip of the needle when the obturator is in the distal position.

4 Claims, 6 Drawing Sheets

INSUFFLATION NEEDLE APPARATUS

BACKGROUND OF THE INVENTION

1. Field of the Invention

This invention relates generally to surgical apparatus and more specifically to a needle apparatus and method for insufflating a body conduit or cavity.

2. Discussion of the Prior Art

In the past, abdominal surgery has been conducted through large open incisions which provide direct access to the interior regions of the abdomen. These open procedures have invited infection, have produced considerable trauma, and have increased recovery time for the patient.

More recently, less invasive procedures have been developed for conducting abdominal surgeries through tubular access devices commonly referred to as trocars. These procedures, which call for the placement of the trocar across the abdominal muscle which defines the abdominal wall, are commonly referred to as laparoscopic procedures. In these delicate operations, small surgical instruments and endoscopes are inserted through working channels of the trocars to perform various surgical functions within the abdominal cavity. The advantages of the less invasive laparoscopic surgeries are well known to include significantly less trauma and reduced healing times. These advantages result from the small puncture wounds associated with the trocars, as opposed to the large incisions associated with open surgery.

In spite of these advantages, laparoscopic surgeries are difficult to perform since the abdominal cavity is maintained substantially intact. Not only does this decrease visibility of the operative site, but it also provides a limited volume within which to manipulate instruments. In order to increase this volume as much as possible, the abdominal cavity is typically inflated or insufflated with carbon dioxide or other gas in order to distend the abdominal wall and increase the volume of the abdominal cavity. This insufflation takes place prior to, as well as during, the laparoscopic surgical procedure. Throughout this entire period, the insufflation gas must be introduced to the cavity in order initially to distend the abdominal wall and ultimately to replace any escaping gas.

In the past, insufflation has been accomplished using needle assemblies having a hollow cylindrical configuration. A needle having a sharpened distal tip is forced through the abdominal wall to provide access to the abdominal cavity through an insufflation channel. Once the sharpened tip is within the abdominal cavity, care must be taken to avoid puncturing internal organs. For this reason an obturator has been provided with the insufflation needle. Once the abdominal wall is penetrated by the needle, a blunt tip of the obturator moves beyond the sharpened tip of the needle to inhibit the further penetration of tissue.

In this configuration, the obturator is also provided with a hollow insufflation channel. This channel extends from the proximal end of the needle assembly through the channel of the obturator to an outlet port at the distal end of the obturator. The outlet port provides communication between the insufflation channel of the obturator and regions exterior of the obturator and needle.

Due primarily to the high costs associated with an operating room, it is of significant advantage to reduce the time during which this insufflation occurs. Often a patient will require as much as three liters of insufflation gas. With a typical insufflation flow rate of 600 milliliters per minute this volume will require five minutes to fully insufflate the cavity. Even a slight reduction in the period of insufflation could significantly reduce operational procedure time and therefore result in a significant cost savings to the hospital and patient.

As noted, it is important that the sharpened distal tip of the needle be isolated from the interior organs immediately upon penetration of the abdominal wall. To accomplish this purpose, the obturator has been biased from a proximal position wherein the sharpened tip is unprotected to facilitate penetration of the abdominal wall, to a distal position where the sharpened tip is isolated to prevent damage to the interior organs. A fast transition from the proximal position to the distal position increases the safety of the insufflation needle. Of course, the speed of this movement between positions is limited by the mass of the obturator. Where the transition has not been sufficiently rapid, momentary exposure of the sharpened tip has tended to damage interior organs.

SUMMARY OF THE INVENTION

In accordance with the present invention, these disadvantages of the prior art have been overcome by providing an insufflation needle apparatus having a significantly increased insufflation gas flow rate and an obturator with a much reduced mass. The flow rate may be increased by, for example, 20% resulting in a one-minute reduction in operational procedure time and a significant increase in cost savings for the hospital. The mass of the obturator is commensurately reduced resulting in a faster transition time between the unprotected proximal position and the protected distal position of the obturator. The faster transition time also produces an audible "click" which communicates the event to the user.

In one aspect, the invention includes an insufflation apparatus with a needle having a lumen and a sharpened distal tip. An obturator disposed within the lumen of the needle has an axis which extends through a proximal section, an intermediate section containing an outlet port, and a distal section. A wall included in the proximal section defines an insufflation channel which communicates with the outlet port. This wall extends along the entire proximal section and has, in a preferred embodiment, a U-shaped, radial cross-section.

In another aspect of the invention, the insufflation apparatus includes a needle having an axis which extends between a proximal end and a distal end. A first wall defines a first lumen which extends along this axis of the needle. An obturator disposed within the first lumen of the needle has a second wall defining a second lumen. An axial portion of this second wall is removed to create a void which extends along substantially the entire length of the obturator. The needle and the obturator define an insufflation channel along the second lumen and the void of the obturator.

In a further aspect, the insufflation apparatus includes a needle having an axis extended between a proximal end and a distal end, and a first wall defining a first lumen extending along the axis of the needle. An obturator disposed within the first lumen of the needle has a second wall which defines a second lumen. First portions of the first wall of the needle and second portions of the second wall of the obturator define an insufflation channel of the apparatus. The first portions of the first wall extend along more than one-half of the length of the needle.

Another aspect of the invention is associated with a method for insufflating a body conduit or cavity. In accordance with this method a needle is provided with a first lumen extending between a proximal end and sharpened distal end. An obturator is inserted into this lumen of the needle. The obturator is provided with a wall defining an insufflation channel and forming at least a portion of a cylinder with an internal radius $r_1$. By removing portions of this wall, the insufflation channel is provided with a cross-sectional area along the entire length of the channel which is greater than $\Pi r_1^2$. This area will typically be less than about $\Pi[r_2^2-\frac{1}{2}(r_3^2-r_1^2)]$ and preferably about $\Pi[r_2^2-\frac{2}{3}(r_3^2-r_1^2)]$, where $r_1$ is the inner radius of the obturator wall, $r_2$ is the radius of the needle lumen, and $r_3$ is the outer radius of the obturator wall. By removing portions of the wall defining the insufflation channel, the cross-sectional area is increased resulting in an increased insufflation rate. Removing the wall portions also reduces the mass of the obturator resulting in a decreased transition time between the proximal position and the distal position of the obturator.

Since the insufflation rate is equal to the cross-sectional area of the insufflation channel, calculated in accordance with the applicable formula set forth above, multiplied by the velocity of flow through the insufflation channel, it follows that an increase in the area is accompanied by a commensurate decrease in the insufflation time.

These and other features and advantages of the invention will be better understood with a description of preferred embodiments and reference to the associated drawings.

DESCRIPTION OF PREFERRED EMBODIMENTS AND BEST MODE OF THE INVENTION

Figure 1:
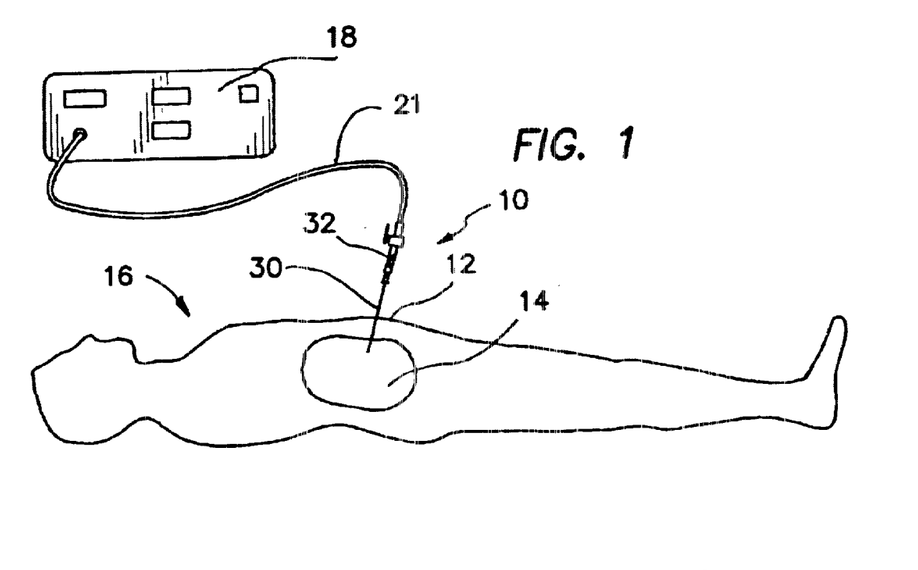
FIG. 1 is a side elevation view of a patient with an insufflation needle apparatus of the present invention operatively disposed to insufflate the abdominal cavity of the patient.

An insufflation needle apparatus is illustrated in FIG. 1 and designated generally by the reference numeral 10. The apparatus 10 is illustrated in operative disposition across an abdominal wall 12 to provide access to an abdominal cavity 14 of a patient 16. Pressurized gas, such as carbon dioxide, from a gas source 18 is introduced through a flexible tube 21 and the insufflation apparatus 10 to pressurize, inflate and distend the abdominal cavity 14 of the patient 16. This enlarges the cavity 14 and thereby facilitates laparoscopic surgeries.

Although the insufflation needle apparatus 10 is particularly adapted for use in laparoscopic procedures, there are other types of surgeries where insufflation gases are used to enlarge various body conduits and other body cavities.

Figure 2:
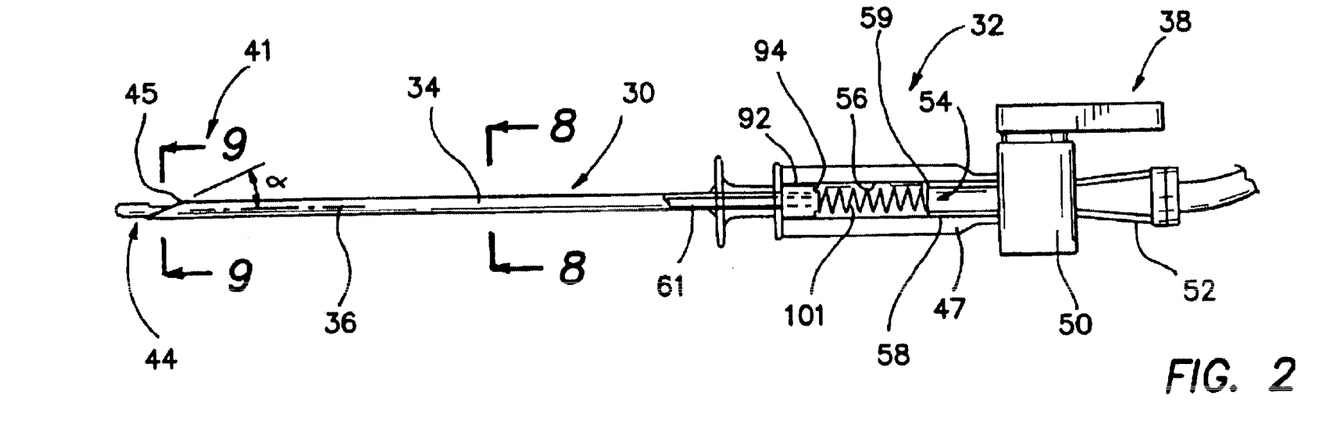
FIG. 2 is a side elevation view partially in section of the insufflation needle apparatus of the present invention.

The insufflation needle apparatus 10 includes an elongate needle 30 extending distally from a handle 32 as best illustrated in the enlarged view of FIG. 2. The needle 30 has a generally hollow cylindrical configuration with a wall 34 extending along an axis 36 between a proximal end 38 and a distal end 41. This wall 34 defines a lumen 43 best illustrated in FIG. 8. A sharpened tip 44 is provided at the distal end 41 of the needle 30. by producing a beveled surface 45 having an acute angle α with the axis 36.

The proximal end of the needle 30 is fixed to the handle 32 which may include a housing 47, a stopcock or valve 50, and a connector 52 for the flexible tube 21. Each of these elements defines part of an insufflation channel 54 which extends consecutively from the gas source 18 through the tube 21, the connector 52, the valve 50, and the housing 47, into the lumen 43 (FIG. 8) of the needle 30.

Within the housing 47, the insufflation channel 54 is defined by an inner cylindrical surface 56, and an insert 58 which has a distally facing shoulder 59.

Figure 3:
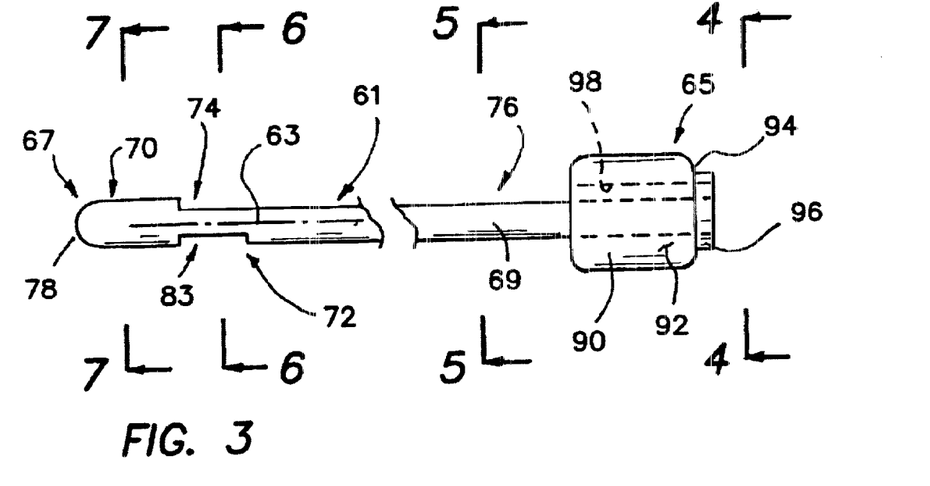
FIG. 3 is a side elevation view showing enlarged distal and proximal ends of an obturator associated with the insufflation apparatus of FIG. 2.
Figure 4:
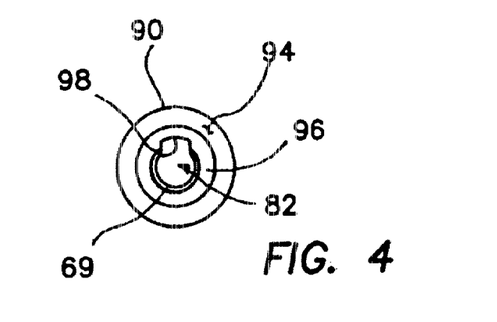
FIG. 4 is a proximal end view of the obturator taken along lines 4—4 of FIG. 3.

Of particular interest to the needle insufflation apparatus 10 is the importance of having some means for isolating the sharpened tip 44 once the abdominal wall 12 (FIG. 1) is penetrated, in order to avoid puncturing interior organs. In a preferred embodiment, this feature is associated with an obturator 61 which is disposed within the lumen 43 of the needle 30. This obturator 61 may have a cylindrical tubular configuration and an axis 63 which extends between a proximal end 65 and a distal end 67 as best illustrated in the detail of FIG. 3.

The obturator 61 in this case is formed from a tube 69 with a distal section 70, an intermediate section 72 having an outlet port 74, and a proximal section 76 extending proximally of the intermediate section 72. In a preferred embodiment, the proximal section 76, extends along more than half the length of the obturator 61. In the distal section 70, the tube 69 is filled or otherwise provided with a blunt distal tip 78. In the intermediate section 72 and proximal section 76, the obturator tube 69 has a generally cylindrical wall 81 defining an interior lumen 82, best illustrated in FIG. 8. Portions of the wall 81 are removed to form the outlet port 74 in the intermediate section 72 and proximal section 76. In the illustrated embodiment, a second outlet port 83 is provided in opposing relationship to the port 74.

At the proximal end of the tube 69, the obturator includes a centering enlargement 90 which has a generally hollow cylindrical configuration in the illustrated embodiment. The enlargement 90 has a cylindrical outer surface 92 and a proximally facing shoulder 94 upon which is center a proximally extending annulus 96. In this embodiment, the wall 81 and interior lumen 82 of the tube 69 extend through the enlargement 90. A recess 98 can be formed in the enlargement 90 to increase the cross-sectional area through which insufflation gases flow. In the preferred position, the obturator 61 is moveable axially between a proximal position, wherein the obturator 61 facilitates exposure of the sharpened tip 44, and a distal position (illustrated in FIG. 2) wherein the obturator 61 covers or isolates the sharpened tip 44.

Between these two positions, the enlargement 90 at the proximate end of the obturator 61 is moveable axially within the housing 47 with its cylindrical surface 92 in sliding engagement with the inner surface 56. A compression spring 101 can be disposed within the housing 47 between the proximally facing shoulder 94 of the enlargement 90 and the distally facing shoulder 59 of the insert 58. This spring 101 tends to bias the obturator 61 to its protective distal position as illustrated in FIG. 2.

When the needle insufflation apparatus 10 is initially inserted through the abdominal wall 12 (FIG. 1) the blunt tip 78 of the obturator 61 is moved proximally against the bias of the spring 101 to expose the sharpened tip 44 of the needle 30. Thus the needle is permitted to penetrate the abdominal wall 12 in order to provide the insufflation channel 54 across the abdominal wall 12. When the sharpened tip 44 penetrates the abdominal wall 12, pressure on the blunt distal tip 78 ceases, and the spring 101 immediately moves the obturator 61 to its protective distal position as illustrated in FIG. 2.

With the obturator 61 operatively disposed in this distal position, insufflation of the abdominal cavity 14 can begin. In the operative position, the tube 69 is disposed within the lumen 43 of the needle 30, so that insufflation takes place primarily through the lumen 82.

Figures 5, 6, 7, 10A:
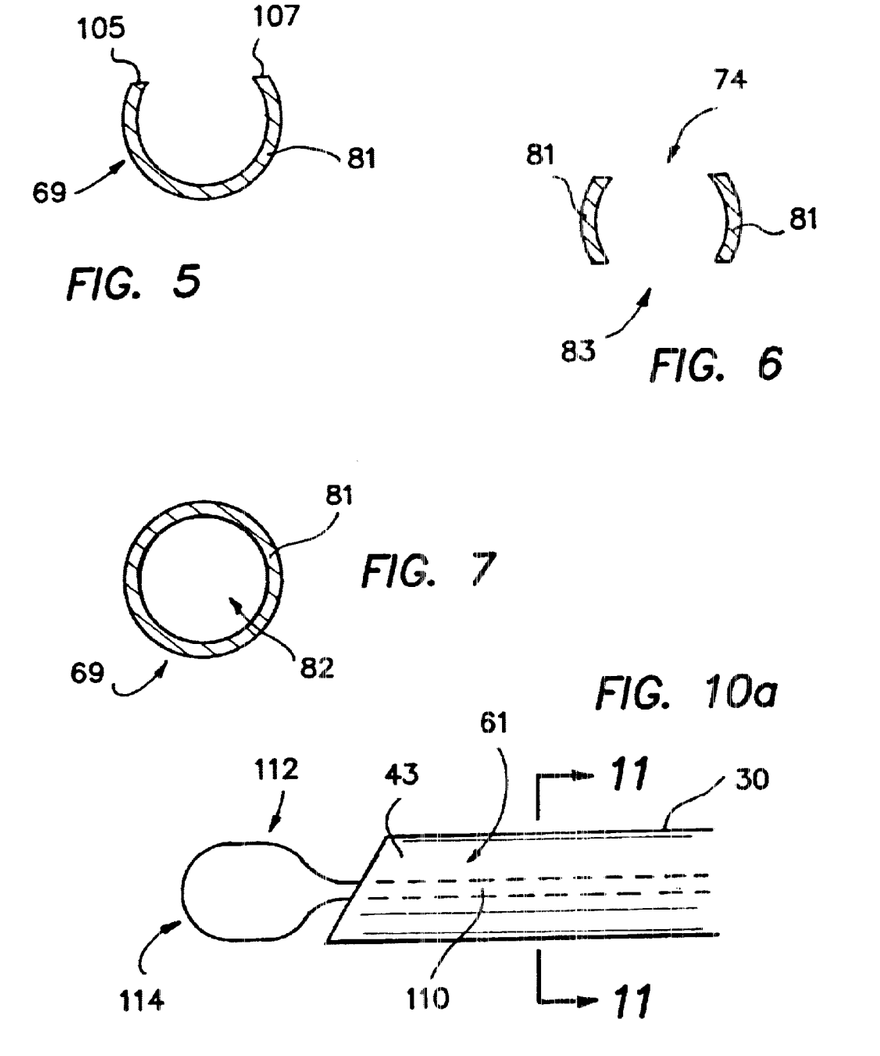
FIG. 5 is a radial cross-section view of the obturator taken along lines 5—5 of FIG. 3.
FIG. 6 is a radial cross-section view taken along lines 6—6 of FIG. 3.
FIG. 7 is a radial cross-section view of the obturator taken along lines 7—7 of FIG. 3.
FIGS. 10a–10f are side elevation views of a needle and an obturator having an extension member and a blunt distal tip.

For reasons previously discussed, it is desirable that the insufflation channel 54 be as large as possible to permit rapid inflation of the abdominal cavity 14 (FIG. 1). In the past, the proximal section 76 of the obturator 61 has been formed as a complete cylinder so that the insufflation channel 54 was restricted to the cross-sectional area of the lumen 82. In accordance with the present invention, this area is dramatically increased by removing a portion of the wall 81. This is accomplished in a preferred method by machining the tube 69 along substantially the entire length of the proximal section 74 to remove a section of the circle forming the cross-section of the wall 81. This provides the cross-section of the wall 81 with a U-shaped configuration where the ends of the U-Shape terminate at machined surfaces 105 and 107 as best illustrated in FIG. 5.

In order that the wall 81 of the obturator 61 might be properly centered within the lumen 43 of the needle 30, it is preferable if the circular cross-section of the wall 81 be left with a circumference greater than 180°. Preferably this circumference should be in a range between 180° and 270°, so that between ½ and ¾ of the circular cross-section of the wall 81 remains. In a preferred embodiment, ⅓ of the wall 81 is removed leaving about 240° or ⅔ of the wall 81.

Figure 8:
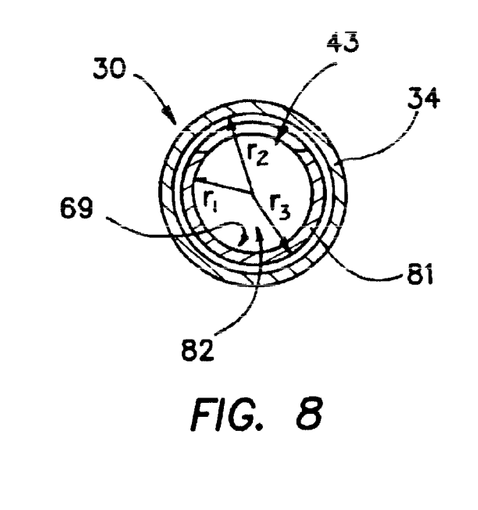
FIG. 8 is a radial cross-section view of the insufflation needle apparatus taken along lines 8—8 of FIG. 2.
Figure 9:
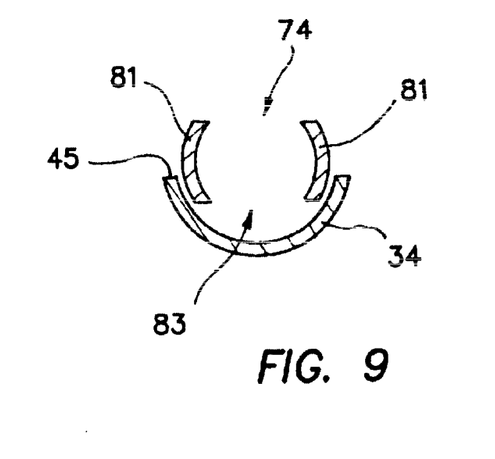
FIG. 9 is a radial cross-section view of the needle insufflation apparatus taken along lines 9—9 of FIG. 2.

Removing a portion of the wall 81 greatly increases the insufflation gas flow rate through the apparatus 10 in a manner best understood with further reference to FIG. 8. In this view, the wall 81 has an inner cylindrical surface with a radius $r_1$. Similarly, the wall 34 of the needle 30 has an inner cylindrical surface with a radius $r_2$. Prior to removing a portion of the wall 81, the insufflation channel 54 is restricted to the cross-sectional area of the lumen 82. This area can be computed in accordance with the well known formula for the area of a circle:

$$A = \Pi r_1^2 \quad \text{(Formula 1)}$$

Where,
  A=cross-section area of the lumen 82
  $r_1$=radius of interior surface of wall 81.

When a portion of the wall 81 is removed, the area of the insufflation channel is increased to a value greater than that computed in accordance with Formula 1. This area can be determined generally in accordance with the following formula:

$$A_s = \Pi[r_2^2 - \beta(r_3^2 - r_1^2)] \quad \text{(Formula 2)}$$

Where,
  $A_s$=the cross-sectional area of the insufflation channel;
  $r_1$=radius of the interior surface of the wall 81;
  $r_2$=radius of the interior surface of the wall 34;
  $r_3$=radius of the exterior surface of the wall 81; and
  $\beta$=the fractional portion of the radial circumference of the wall 81.

It will be noted that the coefficient $\beta$ represents the fractional portion of the radial circumference of the wall 81 which remains after the wall portion is removed. If ½ of the wall 81 remains, the coefficient $\beta$ is equal to ½. When the remaining portion of the wall 81 is greater than 180° in order to facilitate centering of the obturator 61 within the needle 30, the coefficient $\beta$ in Formula 2 may be ⅔, for example.

The mass of the obturator 61 is also reduced in direct proportion to the amount of the wall 81 which is removed. Reducing this mass facilitates the speed with which the obturator can be moved by the spring 101 between its proximal position and its protective distal position.

By removing a portion of the wall 81, the mass of the obturator 61, is significantly reduced. This increases the speed with which the obturator 61 can be moved from its initial proximal position to its safe distal position. This substantially eliminates undesirable organ sticks once the needle 30 penetrates the abdominal wall 12.

Additional embodiments of this concept are illustrated in the side elevation views of FIGS. 10a–10f. In these figures, the obturator 61 is illustrated to include an extension member 110 connected to a distal terminus 112 having a blunt shape at its tip 114. FIGS. 10a–10f illustrate various embodiments of the distal terminus 112, while FIGS. 10a–10p illustrate various embodiments of the extension member 110. These embodiments are merely representative of many different configurations which might be applicable to the distal terminus 112 or the extension member 110.

Figure 10B:
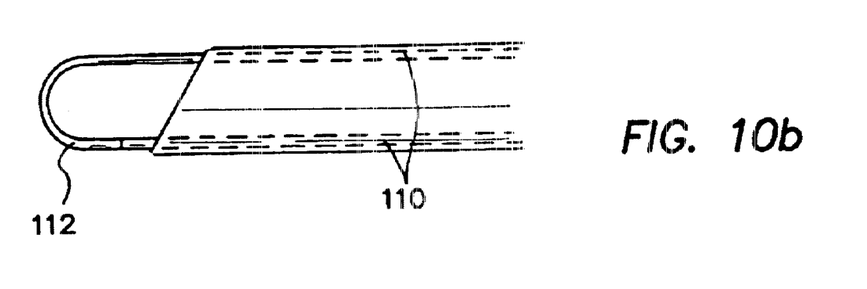
Figure 10C:
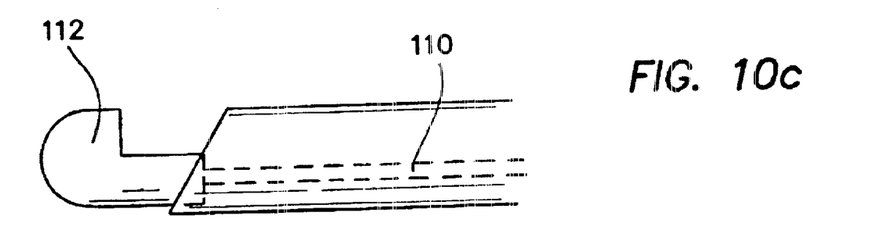
Figure 10D:
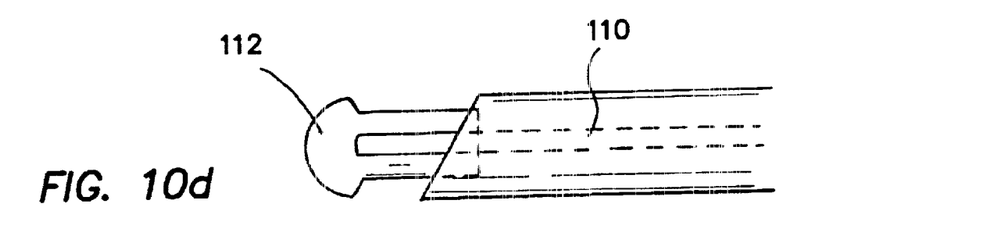
Figure 10E:
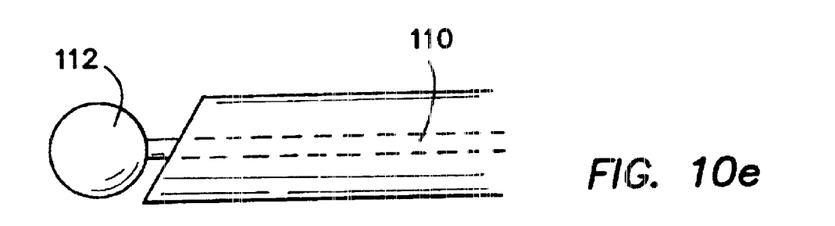
Figure 10F:
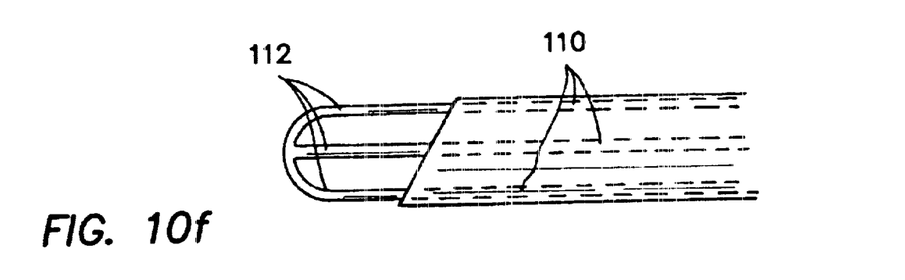

By way of example, it will be noted that the distal terminus 112 illustrated in FIG. 10b and FIG. 10f are provided as wire forms. The wire form in FIG. 10b is two-dimensional, while the wire form 112f is three-dimensional. The distal terminus 112 in FIGS. 10a, 10c, 10d, and 10e can be provided in either a two-dimension or a three-dimension shape. In the two-dimension configuration, the terminus 112 would have more of a spade configuration. Nevertheless, in both of these alternatives, the terminus 112 has a rounded or blunt tip 114. Although the terminus 112 is referred to in some cases as a wire form, it will be appreciated that the terminus 112 can be formed from either a metal or plastic element attached to the extension member 110.

Figure 11A:
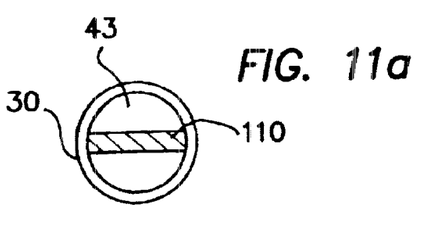
FIGS. 11a–11p are radial cross-section views taken along lines 11—11 of FIG. 10a and illustrating various cross-sectional configurations for the obturator extension member.
Figure 11B:
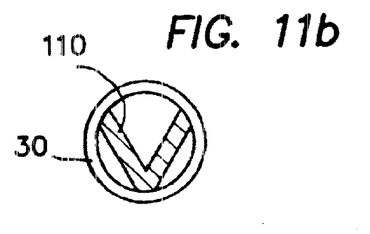
Figure 11C:
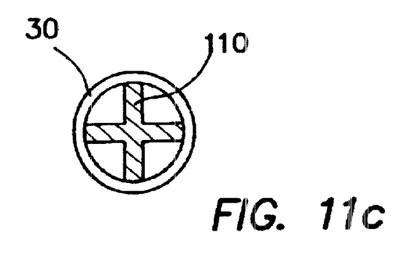
Figure 11D:
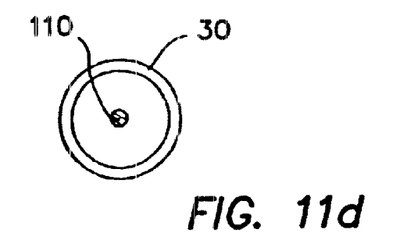
Figure 11E:
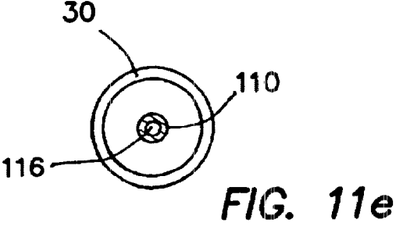
Figure 11F:
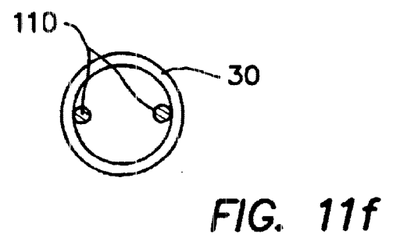
Figure 11G:
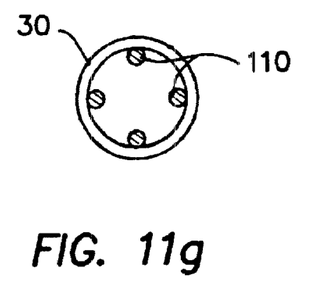
Figure 11H:
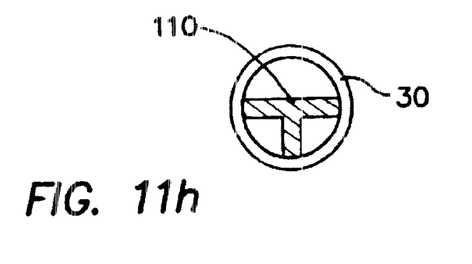
Figure 11I:
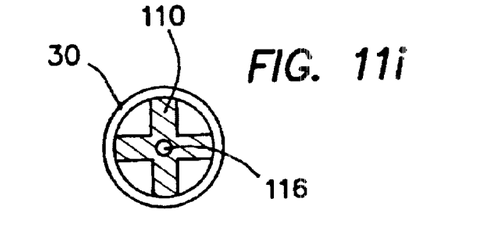
Figure 11J:
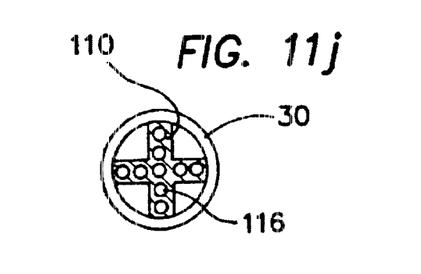
Figure 11K:
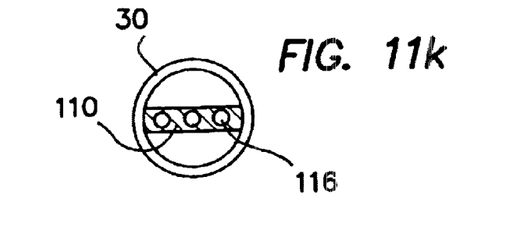
Figure 11L:
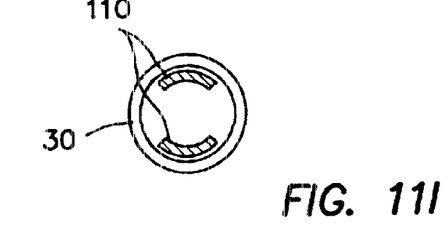
Figure 11M:
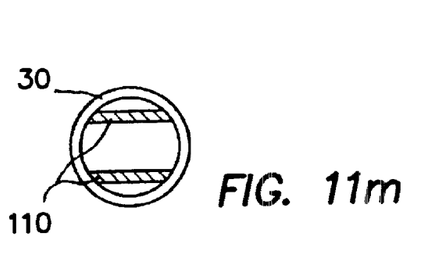
Figure 11N:
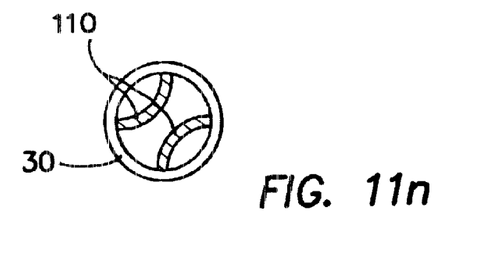
Figure 11O:
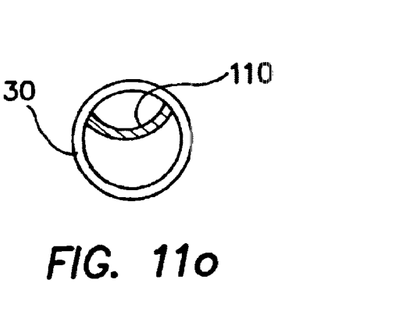
Figure 11P:
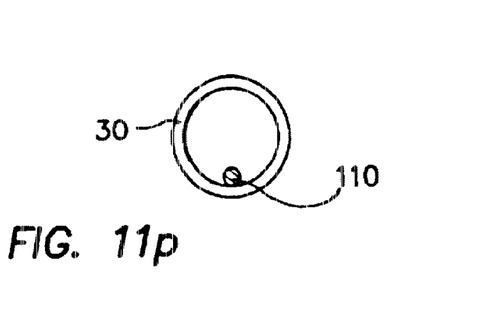

By way of example, FIGS. 11a–11p illustrate various embodiments of the extension member 110. In each of these embodiments, the extension member 110 is elongate in configuration and extends through the lumen of the needle 30 to move the distal terminus 112 axially as previously discussed. In each of the illustrated embodiments, the extension member 110 is reduced in cross-section to occupy but a small portion of the volume of the needle lumen 43. In the manner previously discussed, this significantly increases the cross-sectional area of the insufflation lumen thereby increasing the insufflation rate and decreasing the mass of the obturator 61. From the embodiments of FIGS. 11d, 11f, 11g, and 11p, it will be apparent that the extension member 110 can be provided as a wire form. For example, the extension 110 can be provided as a single wire disposed concentric with the needle 30, as illustrated in FIG. 10d, or in proximity to the needle 30, as illustrated in FIG. 11p. The extension member 110 also can be provided as two wires, as illustrated in FIG. 11f, or four wires, as illustrated in FIG. 11g.

The extension member 110 can also be provided as one or more planar members, as in FIGS. 11a, 11b, 11c, 11h, 11h, 11*j*, 11*k*, and 11*m*. Two planar members can be formed in a V-shape as in FIG. 11*b*, an X-shape as in FIG. 11*c*, or a T-shape as in FIG. 11*h*. Alternatively, the extension member 110 can be formed as two parallel planar members as in FIG. 11*m*.

The extension member 110 can also be formed as one or more curved members as illustrated in FIGS. 11*l*, 11*n*, and 11*o*. The outer surface of these curved members may be convex, as illustrated in FIG. 11*l*, or concave, as illustrated in FIG. 11*n*. Alternatively, the curved extension member 110 may have outer surfaces that are both concave and convex as illustrated in FIG. 11*o*.

In any of these embodiments, the extension member 110 can be provided with longitudinal passages 116, as illustrated in FIGS. 11*e*, 11*i*, 11*j*, and 11*k*. These passages 116 will further reduce the weight of the obturator 61 and facilitate a rapid deployment of the distal terminus 112.

There are many variations on the foregoing concept which are all within the scope of the present invention. For example, it will be noted that any reduction in the mass of the obturator 61 will result in an increased speed of movement from its initial proximal position to its safe distal position. If this mass is removed from the interior surface of the tube 69, there will also be an increase in the cross-sectional area of the insufflation channel 54. If an entire section of the wall 81 is removed, the insufflation channel 54 is expanded to include an area up to the internal surface of the wall 34 of the needle 30. By increasing the cross-sectional area of this channel 54, insufflation times associated with the initial inflation of the abdominal cavity 14 can be significantly decreased resulting in a reduction in the time as well as the cost of the procedure. A higher gas insufflation rate also increases the response time of the insufflation apparatus as the gas pressure is maintained throughout the operative procedure.

Due to these and other variations, one is cautioned not to limit the concept of the embodiments shown and described, but rather, one is encouraged to determine the scope of the invention only with reference to the following.

What is claimed is:

1. An insufflation apparatus adapted to insufflate a body conduit or cavity in a surgical procedure, including:
  a needle having an axis and a first cylindrical wall defining a first lumen extending along the axis of the needle, the first cylindrical wall defining an internal radius $r_2$;
  an obturator disposed coaxially of the needle within the first lumen of the needle, the obturator having a second cylindrical wall defining a second lumen between a proximal end and a distal end of the obturator;
  portions of the second cylindrical wall defining:
    a first void extending from the proximal end of the obturator to a particular location short of the distal end of the obturator, and
    a second void diametrically opposed to the first void and extending only along a distal section of the obturator, the second cylindrical wall defining an external radius $r_3$ and an internal radius $r_1$, the portions of the second cylindrical wall comprising a fractional portion $\beta$ of a radial circumference of the second cylindrical wall; and
    the needle and the obturator defining an insufflation channel along the second lumen and the first and second voids of the obturator, to facilitate gas flow distally in order to inflate and enlarge the body conduit or cavity, the insufflation channel defining a cross section area $A_S$ that is about:

$$A_s = \Pi[r_2^2 - \beta(r_3^2 - r_1^2)],$$

wherein $\beta$ is between ½ and ⅔.

2. An insufflation apparatus adapted to insufflate a body conduit or cavity in a surgical procedure, comprising:
  a needle having an axis and a first cylindrical wall defining a first lumen extending along the axis of the needle, the first cylindrical wall defining an internal radius $r_2$;
  an obturator disposed coaxially of the needle within the first lumen of the needle, the obturator having a second cylindrical wall defining a second lumen between a proximal end and a distal end of the obturator;
  portions of the second cylindrical wall defining:
    a first void extending from the proximal end of the obturator to a particular location more than one-half the length of the obturator, and
    a second void diametrically opposed to the first void and extending only along a distal section of the obturator, the second cylindrical wall defining an external radius $r_3$ and an internal radius $r_1$, the portions of the second cylindrical wall comprising a fractional portion $\beta$ of a radial circumference of the second cylindrical wall; and
    the needle and the obturator defining an insufflation channel along the second lumen and the first and second voids of the obturator, to facilitate gas flow distally in order to inflate and enlarge the body conduit or cavity, the insufflation channel defining a cross section area $A_S$ that is about:

$$A_s = \Pi[r_2^2 - \beta(r_3^2 - r_1^2)],$$

wherein $\beta$ is between ½ and ½.

3. The insufflation apparatus recited in claim 2, wherein said particular location extends along substantially the entire length of the obturator.

4. An insufflation apparatus adapted to insufflate a body conduit or cavity in a surgical procedure, including:
  a source of insufflation fluid under pressure; a needle having an axis and a first cylindrical wall extending between a proximal end and a distal end, the first cylindrical wall defining a first lumen extending axially through the proximal end of the needle in fluid communication with the source of insufflation fluid, the first cylindrical wall defining an internal radius $r_2$;
  an obturator disposed coaxially of the needle in the first lumen of the needle, the obturator having a second cylindrical wall defining a second lumen extending through a proximal section, an intermediate section, and a distal section, the second cylindrical wall having a first void and a second void diametrically opposed to the first void, the first void extending along the proximal section and intermediate section of the obturator, the second void extending only along the distal section and intermediate section of the obturator, the obturator defining an internal radius $r_1$, an external radius $r_3$, and a fractional portion $\beta$ of a radial circumference of the second cylindrical wall;
  and the second cylindrical wall of the obturator forming with the first cylindrical wall of the needle an insufflation channel extending in fluid communication with the source of fluid pressure at the proximal end of the needle to create a flow of the insufflation fluid distally in the insufflation channel in order to inflate and enlarge the body conduit or cavity, the insufflation channel defining a cross section area $A_S$ that is about:

$$A_s = \Pi[r_2^2 - \beta(r_3^2 - r_1^2)],$$

wherein $\beta$ is between ½ and ⅔.

* * * * *